(12) United States Patent
Garland

(10) Patent No.: US 8,087,933 B2
(45) Date of Patent: Jan. 3, 2012

(54) DENTAL MODEL TRAY AND ASSOCIATED ARTICULATOR

(76) Inventor: James K. Garland, Sandy, UT (US)

( * ) Notice: Subject to any disclaimer, the term of this patent is extended or adjusted under 35 U.S.C. 154(b) by 0 days.

(21) Appl. No.: 10/589,386

(22) PCT Filed: Jan. 26, 2005

(86) PCT No.: PCT/US2005/003105
§ 371 (c)(1),
(2), (4) Date: Jun. 7, 2007

(87) PCT Pub. No.: WO2005/082269
PCT Pub. Date: Sep. 9, 2005

(65) Prior Publication Data
US 2008/0026341 A1    Jan. 31, 2008

Related U.S. Application Data

(60) Provisional application No. 60/546,406, filed on Feb. 20, 2004.

(51) Int. Cl.
*A61C 11/00* (2006.01)
(52) U.S. Cl. ............................................. 433/60; 433/61
(58) Field of Classification Search .................... 433/33, 433/54, 74, 213, 214, 57–67; 434/264; D24/128
See application file for complete search history.

(56) References Cited

U.S. PATENT DOCUMENTS

| | | | | |
|---|---|---|---|---|
| 223,157 A * | 12/1879 | McPherson | | 433/60 |
| 3,436,827 A * | 4/1969 | Dew | | 433/34 |
| 4,726,768 A * | 2/1988 | Lee | | 433/34 |
| 5,393,227 A * | 2/1995 | Nooning | | 433/74 |
| 6,149,426 A * | 11/2000 | Singer et al. | | 433/37 |
| 6,217,326 B1* | 4/2001 | Hahn | | 433/74 |
| 2002/0072031 A1* | 6/2002 | Sim | | 433/57 |
| 2002/0102514 A1* | 8/2002 | Huffman | | 433/34 |
| 2004/0166466 A1* | 8/2004 | Honstein et al. | | 433/34 |

* cited by examiner

*Primary Examiner* — Todd Manahan
*Assistant Examiner* — Matthew Nelson
(74) *Attorney, Agent, or Firm* — Terry M. Crellin

(57) ABSTRACT

A dental model tray (12) for use in forming a dental model has a rigid bottom wall (16) and a relatively thin side wall (17) extending upwardly from the perimeter of the bottom wall (16) to form an open-topped cavity which is adapted to receive the dental casting material. The bottom wall (16) and the side wall (17) are formed integrally of polymeric material, with the side wall (17) being joined to or attached to the bottom wall (16) by a thin membrane-like connector member (19) that is formed integrally with the perimeter of the bottom wall (16) and a lower side edge of the side wall (17). The connector member (19) is frangible and easily broken so that the side wall (17) can be torn away from the base and discarded after dental casting material has hardened in the cavity formed by the side wall (17). The dental model tray (12) further includes an ell-shaped articulator member (13,14) that extends from a back side of the bottom wall (16). A distal end of the articulator member (13,14) is adapted to be pivotally connected to a mutually respective distal end of another articulator member (13,14) of a mutually associated dental tray to form a working dental model.

4 Claims, 2 Drawing Sheets

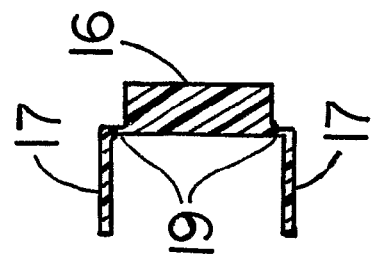
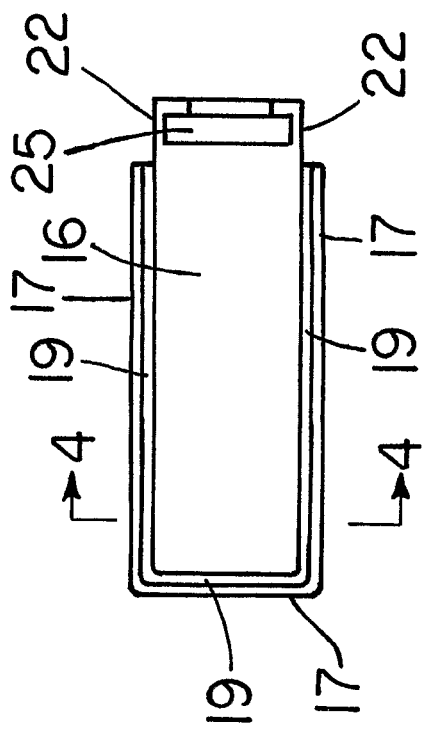
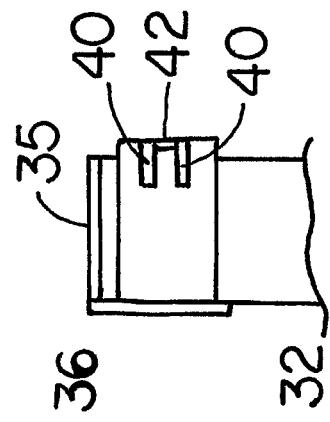

DENTAL MODEL TRAY AND ASSOCIATED ARTICULATOR

PRIORITY

This application claims the priority from U.S. Provisional Patent Application No. 60/546,406 filed on Feb. 20, 2004 and PCT/US05/03105 filed Jan. 26, 2005.

BACKGROUND OF THE INVENTION

1. Field of the Invention

The present invention relates generally to apparatus used in making a dental model from a dental impression whereby the patient's teeth are accurately replicated in the dental model. In particular, the present invention relates to novel trays used in casting the dental models and articulation systems used in association with the trays and the models which are cast in the trays.

2. State of the Art

In order to fabricate a dental prosthetic, such as a crown, inlay, bridge, etc., a negative impression of a patient's teeth is taken using an impression material, and a reproduction of the impression is made as a model in the dental laboratory. The reproduction is a solid, positive model or replication of the gums and at least several adjacent teeth in the mouth of the patient. It is necessary to support the replication or dental model on an articulation device to determine proper size, fit and movement of the restorative prosthetic relative to the other teeth of the patient.

The process of forming dental models is widely known and is described in U.S. Pat. No. 5,207,574 and will not be repeated here. Generally, the reproduction of the patient's teeth corresponding to the upper and lower teeth are formed in separate casting steps. The models of the respective upper and lower teeth are then affixed to an articulation device during the preparation of a restorative prosthetic.

Tray and articulation systems to which the present invention is closely related are shown in U.S. Pat. Nos. 5,846,076 and 5,913,681. In U.S. Pat. No. 5,846,076 a tray is shown having a bottom wall and side walls that extend upwardly from the perimeter of the bottom wall to form an open-topped cavity into which dental casting material is poured. The tray is made of elastomeric material so that the tray can be easily removed from the cast model that is formed in the tray. The tray after being stripped from the cast model is then discarded.

In U.S. Pat. No. 5,913,681 a tray is provided that includes a base wall and upwardly extending side walls at the perimeter of the base wall similar to that of U.S. Pat. No. 5,846,076. However, the tray of U.S. Pat. No. 5,913,681 is formed as a single piece from a non-elastomeric, rigid material, and the cast model must be excised with some difficulty from the tray.

OBJECTIVES AND BRIEF DESCRIPTION OF THE INVENTION

A principal objective of the invention is to provide a novel tray for use in making dental models wherein the tray is made of a rigid polymeric material and has a substantially planar base with upstanding side walls integrally attached at the perimeter of the planar base by an easily ripped or torn, frangible membrane or thin film type connector mechanism that integrally connects the lower edge or perimeter of the side walls to the planar base. In one preferred embodiment, the connector mechanism comprises a thin membrane or film that is integrally formed with the planar base and side walls and of the same polymeric material of the base and side walls. In another preferred embodiment, the film of the connector mechanism is advantageously formed into spaced apart, frangible tabs which are formed integrally with the base and the side walls. The side walls extend upwardly substantially perpendicular to the planar base so as to form an open-topped cavity into which dental casting material can be poured in the process of making a dental model.

The dental casting material is contained within the open-topped cavity and on the planar base of the tray by the upstanding side walls of the tray. After the dental casting material has been formed into the dental model and has set or hardened, the side walls on the tray can be pulled away from the sides of the model and ripped or torn from the perimeter of the planar base of the tray. The connector mechanism, whether formed as frangible tabs or a continuous, frangible, thin membrane that holds the side walls to the planar base is easily ripped or torn so as to remove the side walls. In the embodiment wherein the connector mechanism comprises spaced apart, frangible tabs, the side walls are ripped or torn from the planar base in the fashion of removing one postage stamp from an adjacent stamp. In all instances, the planar base remains firmly attached to the bottom of the dental casting, and dies can be cut in the dental casting from the upper surface of the casting to the planar base as is done in utilizing the dental model in forming a prosthetic device such as an inlay, crown or bridge.

A further objective of the present invention is to provide an improved articulation system to be used with the novel tray. The articulation system of the present invention is an improvement upon the articulation systems shown in U.S. Pat. Nos. 5,913,681 and 5,847,076. The articulation system of the present invention includes an ell-shaped extension that extends from each of the trays which are used in making the dental model. The distal ends of the ell-shaped extensions have a telescopic type attachment such that the end of one extension can be connected to the end of the other extension whereby the extensions can be pivotally rotated relative to each other about the common axis of the telescopic type attachment.

In accordance with one aspect of the present invention, a locking mechanism is provided that locks the telescopic attachment in place so that it can rotate about its common axis but neither part of the telescopic attachment can move longitudinally with respect to the other along the common axis. This allows the dental models formed on the trays to be moved toward and away from each other and from side to side in an occlusion type movement, with the models on each tray being held in the same relationship with each other as the real teeth of the patient are during normal chewing and movement of the jaws of the patient.

Additional objects and features of the invention will become apparent from the following detailed description taken together with the accompanying drawings.

THE DRAWINGS

Preferred embodiments of the present invention representing the best mode presently contemplated of carrying out the invention are illustrated in the accompanying drawings in which:

FIG. 2 is a bottom view of a dental tray of the present invention taken in the direction of line 2-2 of FIG. 1 with the connector mechanism shown in FIG. 2 being a continuous thin membrane that has not been formed into spaced apart tabs as shown in FIG. 1;

FIG. 3 is a partial vertical elevation of the connecting member of one of the articulation members as taken along line 3-3 of FIG. 1; and FIG. 4 is a cross-section taken along line 4-4 of FIG. 2, and it should be recognized that the cross-section of FIG. 4 also represents a similar cross-section taken through a tab of the connector mechanism of FIG. 1.

DETAILED DESCRIPTION OF THE PREFERRED EMBODIMENTS

Figure 1:
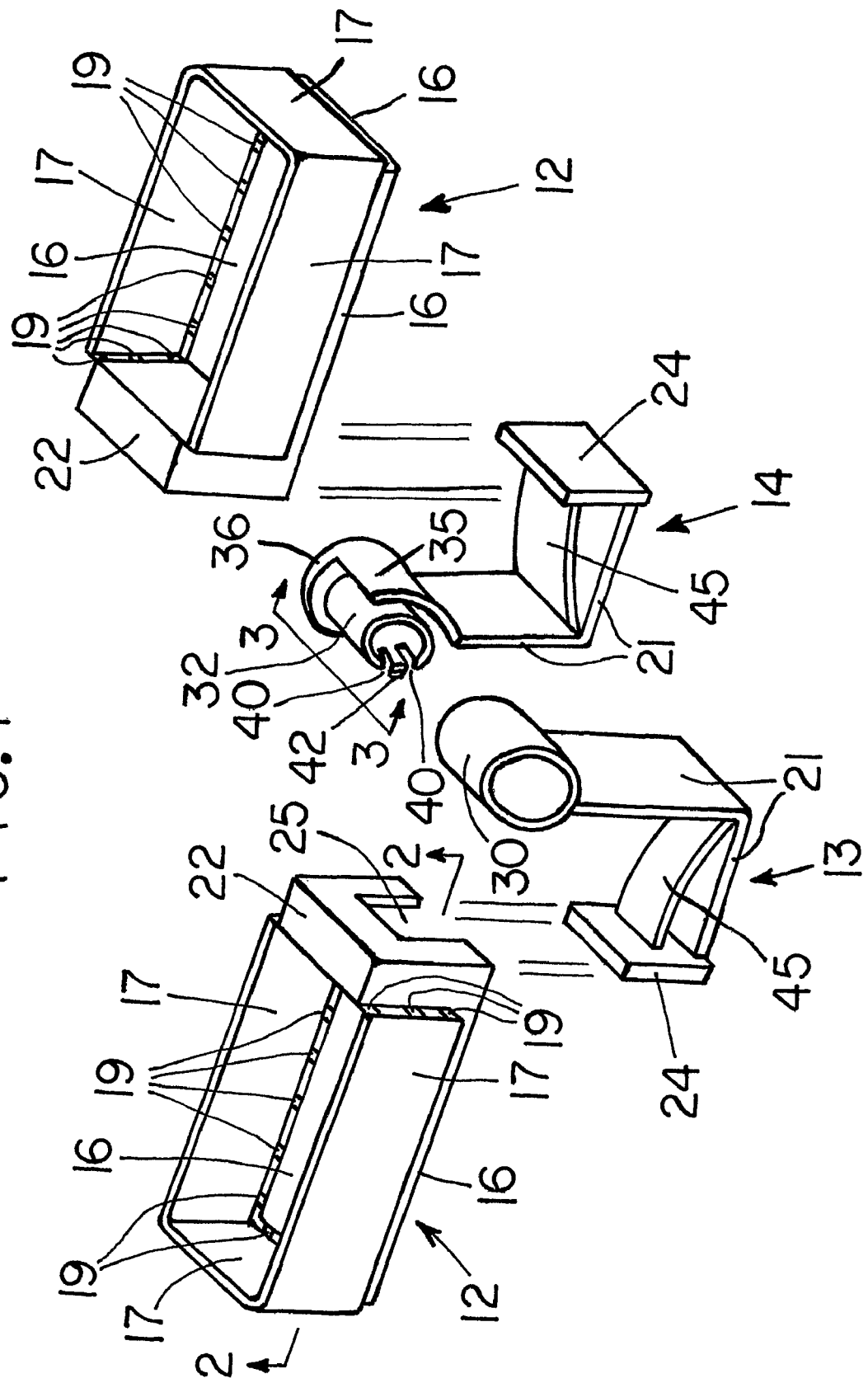
FIG. 1 is an exploded, pictorial representation of two dental model trays in accordance with the present invention, with the dental model trays being associated with a preferred articulation system to show how the trays are associated with the articulation system when they are being used in making a dental model.

Two dental trays 12 and associated articulation members 13 and 14 of the present invention are shown in FIG. 1. The trays 12 are used in pairs as is conventional in the dental modeling art. The two trays 12 shown in FIG. 1 are identical. Each tray 12 comprises a rigid bottom wall 16. A continuous, relatively thin side wall 17 extends upwardly from the perimeter of the bottom wall 16 to form an open-topped cavity which is adapted to receive the dental casting material.

The trays 12 of this invention are formed integrally from a rigid polymeric material. The side wall 17 is attached to the perimeter of the bottom wall 16 by a connector mechanism that comprises a thin, membrane or at least membrane-like member 19 that is formed integrally with both the side wall 17 and the perimeter of the bottom wall 16. The connector member 19 is formed from the same polymeric material as the bottom wall 16 and side wall 17, and the bottom wall 16, the side wall 17 and their associated connector member 19 are formed integrally and simultaneously. The thin membrane-like connector member 19 can be easily ripped or torn apart so that the side wall 17 can readily be removed from the base wall 16 when such is desired.

As illustrated in FIG. 1, the thin membrane-like connector member 19 is formed as a plurality of spaced apart tabs 19 that are integrally formed with the side wall 17 and bottom wall 16. The tabs 19 are made relatively thin so that they are frangible and can easily be broken. The purpose of the frangible tabs 19 is to allow the side wall 17 to be ripped or torn from the bottom wall 16 after the dental casting material has hardened in the tray 12. The spacing between tabs 19 can vary widely from closely spaced tabs to tabs that are spaced relatively far from each other. When the tabs 19 are spaced relatively far from each other, there should be at least about 4 of the spaced apart thin tabs 19 connecting the bottom wall 16 and the lower edge of the side wall 17.

In FIGS. 2 and 3, the thin membrane-like connector member 19 is shown as being a continuous member that extends continuously along the entire length of the edge of the side wall 17 which is connected to the perimeter of the bottom wall 16. Again, the connector member 19 is integrally formed with the side wall 17 and bottom wall 16 and is made relatively thin so that it is frangible and can easily be broken. This allows the frangible connector member 19 to be ripped or torn so as to remove the side wall 17 from the bottom wall 16 after the dental casting material has hardened in the tray 12.

Once the dental casting material has hardened in the trays, the side wall 17 is ripped from the bottom wall 16 to leave the cast stone mounted on the bottom wall 16, and the side wall 17 that has been removed from the cast stone and the bottom wall is then discarded. The stone which includes the replication of the teeth of a person can then be handled in conventional fashion to form dies of the tooth or teeth that a prosthetic is to be prepared for. The dies are formed in conventional fashion by sawing down through the casting from the top of the replicated teeth to near the bottom wall 16 which is still securely secured to the bottom of the dental model.

An articulation system is provided so that occlusion of the upper and lower teeth of the replication can be achieved as is well known in the art. A preferred articulation system of the present invention comprises an ell-shaped member 21 that extends from the back side edge of the bottom wall 16. For this purpose, the back wall 22 of the tray 12 is preferably formed integrally with the back side edge of the bottom wall 16 and extends upwardly substantially perpendicular to the broad upper face of the bottom wall 16. This back wall 22 provides structure to which the ell-shaped member 21 is firmly attached. It should be recognized that the ell-shaped member 21 could be simply attached to the back side edge of the bottom wall 16, but it is preferable to provide the rigid, integral back wall 22 as shown in the drawings.

The ell-shaped member 21 comprises two legs that are joined together at a common juncture and extend from that juncture at an angle of substantially 90 degrees relative to each other. The legs are flat strips having a width of about 3/8 inch to 5/8 inch and a thickness of about 3/64 inch and 5/64 inch. Preferably, the width of the legs is about 1/2 and the thickness is about 1/16 inch.

The ell-shaped member 21 can be formed integrally with the back side edge of the bottom wall 16 or the back, exposed side of the back wall 22, but as shown in the drawings, it is preferable to make the ell-shaped member 21 a distinct, separate piece that is removably attached to the back wall 22. In the embodiment of the invention as shown in the drawings, a first distal end of the ell-shaped member 21 is integrally formed to a slide block 24 which is adapted to be received in sliding manner within a slot-like opening 25 in the back wall 22. As illustrated, an upwardly extending opening 25 is formed in the back wall 22 extending upwardly from the bottom of the back wall 22 to near the top of the back wall 22. The back wall 22 is of sufficient thickness to accommodate the slot-like opening 25 which is in turn of sufficient thickness to receive the block 24 in sliding movement within the slot-like opening 25. The slot-like opening 25 is open at its bottom side on the bottom of the back wall 22, and the top of the back wall forms a stop surface at the inside top of the opening 25.

The block 24 is sized so as to make a snug, semi-tight to tight fit within the slot-like opening 25 as the block 24 slides upwardly through the open end of and into the slot-like opening 25. When the upper end surface of the block 24 engages the stop surface, i.e., the top surface of the slot-like opening 25, the ell-shaped member 21 is positioned in its correct position and the tightness of the fit between the block 24 and the slot-like opening 25 holds the ell shaped member 21 securely in its correct position.

It should be recognized here that when using the system of the present invention, two trays 12 are used on which dental models will be formed with the respective replications of a person's upper and lower teeth. The articulation system is used to hold the two trays and dental models formed thereon so that the replications of the person's teeth can be pivoted in an articulation movement to simulate the occlusion of the upper teeth with the lower teeth. The articulation system of the present invention includes an ell-shaped member 21 for each of the trays 12, and the ell-shaped member 21 as so far described is the same for each of the trays. From here on each of the first and second members of the articulation system will be described independently inasmuch as there are differences in the two members. The first member is shown by the numeral 13 in the drawings and the second member by the numeral 14. Again, both the first and second members 13 and 14 each comprise an ell-shaped member 21 having first and second legs with a slide block 24 attached at a distal end of a first leg of the ell-shaped member as previously described.

The second distal end of the ell-shaped member 21 of the first member 13 of the articulation system has a cylinder 30 attached thereto. The cylinder has a length that is substantially the same as the width of the leg of the ell-shaped member 21. The exterior surface of the cylinder 30 is joined to the distal end of the ell-shaped member 21 so that the axis of the cylinder 30 is parallel with the plane of the leg of the ell-shaped member to which the cylinder 30 is attached. In addition, the cylinder 30 is so attached to the distal end of the ell-shaped member 21 such that the axis of the cylinder 30 is displaced just slightly away from the exterior face of the leg of the ell-shaped member 21. The thickness of the wall of the cylinder 30 is substantially the same as the thickness of the leg of the ell-shaped member 21.

The second distal end of the ell-shaped member 21 of the second member 14 of the articulation system also has a cylinder 32 attached thereto. The cylinder 32 has a length that is slightly longer than the length of cylinder 30 of the first member 13. The cylinder 32 is of an exterior size such that it can smoothly fit longitudinally within the cylinder 30 of the first member 13 of the articulation system. The cylinder 32 is specially attached to the distal end of the ell-shaped member 21 of the second member 14 so that the cylinder 32 can be received coaxially within the cylinder 30 of the other member 13, and when the cylinder 32 is so received coaxially within the cylinder 30, the respective ell-shaped members 21 to which the cylinders 30 and 32 are attached are positioned with the two members 13 and 14 and the first and second legs of the ell-shaped members 21 lying in a common central plane whereby each of the two members 13 and 14 can rotate or pivot in that common plane about the common axis of the coaxially positioned cylinders 30 and 32.

The means for joining the cylinder 32 to it respective ell-shaped member 21 comprises forming a circular extension 35 at the second distal end of the ell-shaped member 21 of the second member 14 of the articulation system. This circular extension 35 is adapted to nest outwardly and over the exterior surface of the cylinder 30 of the first member 13 of the articulation system when the cylinders 30 and 32 are engaged coaxially. A back plate 36 is attached at the back edge of the circular extension 35, and the cylinder 32 extends outwardly generally perpendicular from the back plate 36. The axis of the cylinder 32 is parallel with the plane of the leg of the ell-shaped member to which the cylinder 32 is attached. In addition, the cylinder 32 is so attached to the ell-shaped member 21 such that the axis of the cylinder 32 is displaced just slightly away from the exterior face of the leg of the ell-shaped member 21. The thickness of the wall of the cylinder 32 is substantially the same as the thickness of the leg of the ell-shaped member 21.

A locking device is provided that locks the two cylinders 30 and 32 in their operating position so that the cylinders can pivot about their common axis but will not move longitudinally with respect to each other during the pivoting movement. The longitudinal length of the cylinder 32 is slightly longer than the corresponding length of the cylinder 30. When the cylinder 32 is received within the cylinder 30, the end of cylinder 30 abuts directly against the back plate at the end of cylinder 32, and the free end of cylinder 32 extends slightly from the other end of cylinder 30. As shown in FIG. 3, a pair of slots 40 are cut in the free end of the cylinder 32. The slots 40 are spaced close to each other generally between about 1/16 inch and 3/32 inch apart. The longitudinal length of the slots 40 are between about 1/8 inch and 5/32 inch long. A small projection or tab 42 extends outwardly from the outer surface of the cylinder 32 adjacent to the free end of the cylinder 32 and between the slots 40.

When the free end of the cylinder 32 is pushed into the engaging end of the cylinder 30, the tab 42 is pushed inwardly which is allowed because of the bending of the portion of the cylinder 32 between the slots 40. When the tab 42 clears the other end of the cylinder 30 it snaps out against the end of the cylinder 30 and prevents the cylinder 32 from moving longitudinally back within the cylinder 30. At the same time, the other end of the cylinder 30 has engaged the back plate 36 on cylinder 32. Thus the cylinders 30 and 32 are locked in place relative to longitudinal movement but are free to make their pivotal movement about their common axis.

The locking device on the cylinders 30 and 32 guarantee that the replications of the upper and lower teeth of the dental model can be pivoted toward and away from each other with the upper and lower teeth always being located properly in vertical alignment. The locking mechanism of the cylinders 30 and 32 prevents the displacement of the upper model and the lower model out of their proper position one directly in alignment with the other.

There are certain movements that are desired and achieved with the articulation mechanism of the present apparatus. The pivoting motion as explained above is one. But in addition to the pivoting movement it is very beneficial and necessary that the laboratory technician when making a prosthetic for a tooth is able to grind the teeth of the model back and forth in a horizontal direction in both a forward and backward movement as well as a side to side movement. The articulation mechanism of the present invention provides for both of these additional movement. Each of the members 13 and 14 of the articulation device are preferably molded from a polymeric material wherein all the individual elements are molded integrally with each other. The flexibility of the legs of the ell-shaped members 21 to which the cylinders 30 and 32 are attached allow for forward and backward movement of the models to simulate forward and backward grinding of the teeth. In addition, the flexibility of these legs allows for back and forth motion of the models to simulate back and forth grinding of the teeth.

There is one movement that is to be avoided, and the articulation device of the present invention prevents that movement. The movement that is to be avoided is a rocking or rolling movement of the teeth in one of the dental models with respect to the teeth in the other model. What is to be avoided is any motion of the type in which the dental models can pivot about a longitudinal axis through the models. It has been unexpectedly found that by providing a stabilizer wall 45 that extends from the block 24 to the apex of the legs of the ell-shaped members 21 will stabilize the ell-shaped members 21 against this type of rocking and rolling motion. The dual walls which are formed by the one leg of the ell-shaped member 21 and the stabilizer wall 45 prevent axial rotation about the central axis of the ell-shaped member 21 through the leg of that member that connects the block 24 to the other leg of that member. It has been found that the first end of the stabilizer wall 45 should extend from a position on the block 24 that is spaced from the intersection of the leg of the ell-shaped member 21 and the block 24 to the apex of the intersection of the two legs of the ell-shaped member 21. The stabilizer wall 45 prevents any distortion of the leg of the ell-shaped member 21 that is connected to the block 24. If the stabilizer wall 45 extends straight across from the block 24 to the other leg of the ell-shaped member 21, that other leg is made to rigid to allow the torsional flexing thereof which permits the dental models to be moved in their sideward grinding motion.

The invention claimed is:

1. A dental model tray that is made entirely of a polymeric material and is used in forming a dental model from casting material poured on said tray, said dental model tray comprising
  a substantially planar base that forms the floor upon which dental casting material is poured in forming a dental model;
  a side wall extending upwardly from a perimeter of said base so as to form a cavity having an open top facing upwardly from said base;
  a thin, membrane-like connector member which is formed integrally with the perimeter of said base and a lower side edge of said side wall and thus connects the perimeter of said base with the lower side edge of said side wall, said connector member being frangible and easily broken so that said side wall can be torn away from said base and discarded after dental casting material has hardened in said cavity formed by said side wall;
  an ell-shaped member that extends from a back side of said base;
  said ell-shaped member comprising first and second legs that are joined together at a common iuncture and extend from said iuncture at an angle of substantially 90 degrees relative each other;
  a distal end of said first leg of said leas being attached to said back side of said base such that said one leg extends from said base so that said one leg lies in a plane that is parallel to a planar upper surface of said base;
  each of said first and second legs is formed in the shape of a flat strip having a width of about ⅜ inch to ⅝ inch and a thickness of about 3/64 inch to 5/64 inch;
  means associated with a distal end of said second leg of said ell-shaped member for removably engaging a corresponding distal end of a second leg of a mutually respective similar ell-shaped member of another mutually respective similar dental model tray so that the second legs which are so engaged at their distal ends can pivot about those engaged distal ends in a common plane containing said first and second legs of said engaged ell-shaped members;
  means for removably attaching said distal end of said first leg to said base comprising;
  a slide block integrally formed at said distal end of said one leg;
  a back wall extending upwardly from said back side of said base;
  an upwardly extending slot-like opening in said back wall of said base, said upwardly extending slot-like opening adapted to receive in snug sliding manner said slide block of said distal end of said one leg so as to firmly hold said one leg in firm engagement with said back wall of said base; and
  a stabilizer wall extending from said common juncture of said first and second legs to a position on said block that is spaced from the intersection of said block and said first leg.

2. The dental model tray in accordance with claim 1 wherein said connector member extends continuously along the entire length of the lower edge of said side wall which is connected to the perimeter of said base.

3. The dental model tray in accordance with claim 1 wherein said connector member is formed as a plurality of spaced apart thin tabs which interconnect said base with said lower edge of said side wall.

4. The dental model tray in accordance with claim 3 wherein there are at least about 4 of said spaced apart thin tabs which interconnect said base with said lower edge of said side wall.

* * * * *